US011419827B2

(12) United States Patent
Harvey et al.

(10) Patent No.: US 11,419,827 B2
(45) Date of Patent: Aug. 23, 2022

(54) PROTECTING TISSUE AND MITIGATING INJURY FROM RADIATION-INDUCED IONIZING EVENTS (71) Applicant: Humanetics Corporation, Edina, MN (US)

(72) Inventors: Adam J. Harvey, Minneapolis, MN (US); Michael D. Kaytor, Maplewood, MN (US); John C. Dykstra, Minneapolis, MN (US)

(73) Assignee: Humanetics Corporation, Minneapolis, MN (US)

( * ) Notice: Subject to any disclaimer, the term of this patent is extended or adjusted under 35 U.S.C. 154(b) by 0 days.

(21) Appl. No.: 16/488,325

(22) PCT Filed: Feb. 23, 2018

(86) PCT No.: PCT/US2018/019507
§ 371 (c)(1),
(2) Date: Aug. 23, 2019

(87) PCT Pub. No.: WO2018/156946
PCT Pub. Date: Aug. 30, 2018

(65) Prior Publication Data
US 2019/0380972 A1 Dec. 19, 2019

Related U.S. Application Data (60) Provisional application No. 62/463,340, filed on Feb. 24, 2017.

(51) Int. Cl.
*A61K 9/51* (2006.01)
*A61P 39/00* (2006.01)
*A61K 31/353* (2006.01)

(52) U.S. Cl.
CPC .......... *A61K 9/5138* (2013.01); *A61K 31/353* (2013.01); *A61P 39/00* (2018.01)

(58) Field of Classification Search
None
See application file for complete search history.

(56) References Cited

U.S. PATENT DOCUMENTS

| | | |
|---|---|---|
| 3,465,153 A | 9/1969 | Libby |
| 6,094,760 A | 8/2000 | Nonka |
| 8,551,530 B2 | 10/2013 | Elder |
| 9,084,726 B2 | 7/2015 | Egberg |
| 11,129,894 B2 | 9/2021 | Harvey et al. |
| 2005/0070508 A1 | 3/2005 | Lou |
| 2005/0090509 A1 | 4/2005 | Lou |
| 2007/0293458 A1 | 12/2007 | Shamsuddin |
| 2009/0263331 A1 | 10/2009 | Wu |
| 2013/0053362 A1 | 2/2013 | Castro |
| 2013/0137916 A1* | 5/2013 | Goer ................. A61K 41/0038 600/1 |
| 2014/0045950 A1 | 2/2014 | Lacko |
| 2014/0341802 A1 | 11/2014 | North |
| 2015/0126597 A1 | 5/2015 | Kaytor |
| 2016/0078167 A1 | 3/2016 | Rosner |
| 2019/0099491 A1 | 4/2019 | Harvey |

FOREIGN PATENT DOCUMENTS

EP 2832356 2/2015

OTHER PUBLICATIONS

Cengel et al., "Oncogenic K-Ras signals through epidermal growth factor receptor and wild-type H-Ras to promote radiation survival in pancreatic and colorectal carcinoma cells," Neoplasia 9(4): 341-348, 2007.
Cucinotta and Durante, "Risk of Radiation Carcinogenesis," In: McPhee and Charles (Eds.), Human Health and Performance Risks of Space Exploration Missions, NASA, pp. 119-170, 2009.
Cucinotta et al., "The effects of delta rays on the number of particle-track traversals per cell in laboratory and space exposures," Rad Res, 150: 115-119, 1998.
Hassler et al., "Mars' surface radiation environment measured with the Mars Science Laboratory's Curiosity rover.," Science 343(6169), DOI: 10.1126/science.1244797, 2014.
International Search Report and Written Opinion in International Application No. PCT/US2018/019507, dated Apr. 26, 2018, 13 pages.
Kruk et al., "Scavenging of reactive oxygen species by the plant phenols genistein and oleuropein," Luminescence: J Biol. Chem. Luminescence 20(2): 81-89, 2005.
Kuiper et al., "Interaction of estrogenic chemicals and phytoestrogens with estrogen receptor beta," Endocrinol 139(10): 4252-4263, 1998.
Liu et al., "Lung cancer cell line screen links Fanconi anemia/BRCA pathway defects to increased relative biological effectiveness of proton radiation," Radiation Oncology 91(5):1081-1089, 2015.
Loboda et al., "A gene expression signature of RAS pathway dependence predicts response to PI3K and RAS pathway inhibitors and expands the population of RAS pathway activated tumors," BMC Medical Genomics, 3: 26, 2010.
Polkowski and Mazurek, "Biological properties of genistein. A review of in vitro and in vivo data," Acta. Poloniae Pharmaceutica—Drug Research 57(2): 135-155, 2000.
Raffoul et al., "Genistein inhibits radiation-induced activation of NF-kappaB in prostate cancer cells promoting apoptosis and G2/M cell cycle arrest," BMC Cancer 6: 107, 2006.

(Continued)

*Primary Examiner* — Jessica Worsham
(74) *Attorney, Agent, or Firm* — Fish & Richardson P.C.

(57) ABSTRACT

Materials and methods for reducing, preventing, or mitigating the effects of exposure to ionizing radiation are provided herein. In general, the methods can include administering a nanoparticulate genistein composition to a subject identified as having been exposed or at risk of being exposed to ionizing radiation, such as proton radiation.

20 Claims, 7 Drawing Sheets (56) References Cited

OTHER PUBLICATIONS

Saleemuddin et al., "Risk factors for a serous cancer precursor ("p53 signature") in women with inherited BRCA mutations," Gynecol Oncol., 111(2): 226-232, 2008.

Sridharan et al., "Understanding cancer development processes after HZE-particle exposure: roles of ROS, DNA damage repair and inflammation," Radiation Res 183: 1-26, 2015.

Verdrengh et al., "Genistein as an anti-inflammatory agent," Inflammation Res. 52(8): 341-346, 2003.

Wu et al., "Risk of acute radiation syndromes due to solar particle events," In: McPhee and Charles (Eds.), *Human Health and Performance Risks of Space Exploration Missions*, NASA, pp. 171-190, 2009.

Zhang et al., "Genistein induces G2/M cell cycle arrest and apoptosis via ATM/p53-dependent pathway in human colon cancer cells," Int. J Oncol. 43(1): 289-296, 2013.

U.S. Appl. No. 16/145,787, filed Sep. 28, 2018, Harvey.

Zhang et al., "Combined treatment of ionizing radiation with genistein on cervical cancer HeLa cells," Journal of pharmacological sciences, Jan. 1, 2006, 102(1):129-135.

International Preliminary Report on Patentability in International Appln. PCT/US2018/019507, dated Sep. 6, 2019, 8 pages.

\* cited by examiner

PROTECTING TISSUE AND MITIGATING INJURY FROM RADIATION-INDUCED IONIZING EVENTS

CROSS-REFERENCE TO RELATED APPLICATIONS

This application is a National Stage Application under 35 U.S.C. § 371 and claims the benefit of International Application No. PCT/US2018/019507, filed on Feb. 23, 2018, which claims benefit of priority from U.S. Provisional Application Ser. No. 62/463,340, filed on Feb. 24, 2017.

TECHNICAL FIELD

This document relates to materials and methods for reducing, preventing, or mitigating acute and chronic biological effects of exposure to ionizing radiation.

BACKGROUND

Exposure to ionizing radiation can have detrimental effects on cells and the organisms containing the cells. For example, acute radiation syndrome (ARS) is an illness caused by irradiation of the body (either the entire body or a significant portion thereof) to ionizing radiation. ARS includes four phases: a prodromal period, a latent period, and a period of illness, followed by recovery or death. During the prodromal period, individuals can experience loss of appetite, nausea, vomiting, fatigue, and diarrhea, and additional symptoms such as fever and respiratory distress may occur after exposure to extremely high doses. These symptoms typically disappear after a day or two, and a symptom-free period follows, with a length depending on the size of the radiation dose. The third period, overt illness, can include characteristics such as infection, electrolyte imbalance, diarrhea, bleeding, and cardiovascular collapse. Finally, death or recovery follows the illness. Delayed effects of acute radiation syndrome (DEARE) also can occur from non-lethal but high acute doses of ionizing radiation. Symptoms are largely tissue-specific, but generally manifest as degenerative diseases, including cardiovascular disease, cognitive impairment, and fibrosis of various tissues, for example. Acute or chronic exposure to low doses of radiation also is a concern. Low doses of radiation, while not being acutely toxic, may still cause irreparable genomic mutations that can increase the risk of cancer later in life, as well as the risk of cardiovascular disease, tissue fibrosis, inflammation, and neurodegenerative conditions.

SUMMARY

This document is based, at least in part, on the discovery that compositions containing genistein can be useful as countermeasures against the ionizing effects of radiation, and particularly against the ionizing effects of neutron and charged particle radiation. Genistein has significant cell-signaling activities that affect how cells respond to radiation damage. As described herein, compositions (e.g., suspension formulations) that contain genistein nanoparticles as the active ingredient may be used as countermeasures against exposure to ionizing radiation, decreasing DNA damage, oxidation, and other adverse effects. In some embodiments, therefore, the methods described herein can be used to mitigate acute and delayed effects in individuals exposed to radiation that induces ionizing events. In some embodiments, the methods described herein also can be used to protect individuals at risk of exposure to radiation that induces ionizing events, preventing or reducing the adverse effects should exposure to such radiation occur.

In one aspect, this document features a method for preventing, reducing, or mitigating, in a subject in need thereof, one or more effects of exposure to proton radiation. The method can include administering to the subject a composition containing nanoparticulate genistein, where the subject is identified as having been exposed to proton radiation or as being at risk of exposure to proton radiation, and where the composition has a nanoparticulate genistein concentration between about 250 mg/mL and about 500 mg/mL. The subject can be a human (e.g., a cancer patient who will undergo proton radiation therapy, an individual who will be traveling to outer space, a first responder, or a member of the military). The genistein nanoparticulate composition can have a particle size distribution characterized by a d(0.5) less than or equal to 0.3 µm. The composition further can contain one or more pharmaceutically acceptable excipients forming a suspension medium, where the one or more pharmaceutically acceptable excipients include a water soluble polymer containing a polyvinylpyrrolidone. The one or more pharmaceutically acceptable excipients can include a nonionic surfactant, a diluent, or a buffer. The nonionic surfactant can be present in an amount ranging from about 0.01% to about 10% by weight (w/w). The amount of water soluble polymer can be about 0.5% to about 15% (w/w). The composition can contain a diluent and a preservative, and optionally can further comprise a non-ionic surfactant. The nanoparticulate genistein can be present in the composition at an amount ranging up to about 50% (w/w), or at an amount of about 20% to about 35% (w/w). The composition can have a nanoparticulate genistein concentration of about 325 mg/mL. The composition can have a pH of about 2 to about 12. The composition can be formulated as a tablet, a capsule, or a gel cap.

The method can include administering the composition orally, intramuscularly, subcutaneously, or intravenously. The method can include administering the composition about 2 hours before potential exposure to the proton radiation, within about 48 hours before potential exposure to the proton radiation, or within about 24 hours before potential exposure to the proton radiation. The can include administering the composition on a daily basis. The method can include administering the composition at a dose of about 0.5 g to about 2.5 g, or at a dose of about 1 g to about 1.5 g. The method can include administering the composition within about 60 minutes after exposure to the proton radiation, or within about 24 hours after exposure to the proton radiation. The method can include administering the composition at a dose of about 0.5 g to about 2.5 g per day for about 1 day to about 90 days.

In another aspect, this document features the use of a composition containing nanoparticulate genistein for preventing, reducing, or mitigating, in a subject in need thereof, one or more effects of exposure to proton radiation, wherein the subject is identified as having been exposed to proton radiation or as being at risk of exposure to proton radiation, and wherein the composition has a nanoparticulate genistein concentration between about 250 mg/mL and about 500 mg/mL. The subject can be a human. The subject can be a cancer patient who will undergo proton radiation therapy, a subject who will be traveling to outer space, a first responder, or a member of the military. The genistein nanoparticulate composition can have a particle size distribution characterized by a d(0.5) less than or equal to 0.3 µm. The composition can further contain one or more pharmaceutically acceptable excipients forming a suspension medium, wherein the one or more pharmaceutically acceptable excipients include a water soluble polymer comprising a polyvinylpyrrolidone. The one or more pharmaceutically acceptable excipients can include a nonionic surfactant, a diluent, or a buffer. The nonionic surfactant can be present in an amount ranging from about 0.01% to about 10% by weight (w/w). The amount of water soluble polymer can be about 0.5% to about 15% (w/w). The composition can contain a diluent and a preservative. The composition can further contain a non-ionic surfactant. The nanoparticulate genistein can be present in the composition at an amount ranging up to about 50% (w/w), or at an amount of about 20% to about 35% (w/w). The composition can have a nanoparticulate genistein concentration of about 325 mg/mL. The composition can have a pH of about 2 to about 12. The composition can be formulated as a tablet, a capsule, or a gel cap. The composition can be formulated for oral, intramuscular, subcutaneous, or intravenous use. The composition can be formulated for administration about 2 hours before potential exposure to the proton radiation, formulated for administration within about 48 hours before potential exposure to the proton radiation, or formulated for administration within about 24 hours before potential exposure to the proton radiation. The composition can be formulated for administration on a daily basis. The composition can be formulated for administration at a dose of about 0.5 g to about 2.5 g, or at a dose of about 1 g to about 1.5 g. The composition can be formulated for administration within about 60 minutes after exposure to the proton radiation, or for administration within about 24 hours after exposure to the proton radiation. The composition can be formulated for administration at a dose of about 0.5 g to about 2.5 g per day for about 1 day to about 90 days.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 is a schematic depicting how genistein may mitigate the deleterious effects of ionizing radiation. For example, x-rays generally mediate their damaging effects via indirect/oxidative effects, as the ionization of water can create reactive oxygen species (ROS). Free radical scavenging by genistein may prevent this damage. Particle radiation involving α particles, β particles, neutrons, and protons typically causes moderate amounts of both indirect and direct damage, while high energy nuclei (HZE) radiation exerts the majority of its negative consequences via direct effects. The physical properties of these particles tend to cause a significant amount of secondary ionization events (delta rays) that concentrate the damage caused by the radiation along the beam path. Thus, on a per-beam (or dose-equivalent) manner, one transit of a cell by HZE radiation can have devastating consequences on the cellular components. These direct effects may be mitigated by genistein. Genistein's affinity for estrogen receptor type β (ERβ) over ERα generally is antagonistic to ER signaling, and suppresses growth pathways in favor of activating cellular checkpoints, which can give cells sufficient time to enact DNA repair. This may be replicated by genistein's tyrosine kinase inhibition, which also is causative of delaying the cell cycle in favor of DNA repair following cellular damage.

FIGS. 4A, 4B, and 4C are graphs plotting the levels of CXCL1 cytokine (FIG. 4A), granulocyte colony stimulating factor (G-CSF; FIG. 4B), and tumor necrosis factor alpha (TNFα; FIG. 4C) in blood from mice injected with 200 mg/kg genistein (s.c.) 24 hours prior to exposure to 6 Gy high LET proton radiation. In these experiments, blood was drawn from mice on the indicated days following radiation exposure, and the levels of cytokines were assayed.

DETAILED DESCRIPTION

As used herein, the term "ionizing radiation" refers to forms of radiation that can induce ionizing events within a cell. Individuals may encounter various forms of ionizing radiation, including alpha, beta, neutron, gamma, proton, and x-ray radiation. Ionizing radiation forms ions in cells of the tissues through which it passes, by removing electrons from atoms and molecules. Different types of radiation have varying levels of energy—typically, the more energy a type of radiation has, the more deeply it can penetrate into tissue.

Each type of ionizing radiation has a typical source. For example, alpha, beta, and gamma radiation are all created by the natural process of radioactive decay. Neutron radiation generally is caused by atomic fission or fusion, and may be encountered in nuclear power plants, in cosmic or high-altitude flight, or from industrial radioactive sources. X-rays are man-made and are generated for clinical purposes.

The physical properties of radiation and their sources underlie the distinction between the various types. For example, gamma rays are high energy photons, and have no appreciable mass or charge. X-rays also are high energy photons, but are distinguished by their source since they are generally created by man-made instruments. In contrast, non-gamma types of ionizing radiation consist of various atomic particles, including neutrons, protons, alpha particles, beta particles, and high energy nuclei (HZE), and have distinct physical properties, including the mass of each particle. Because these non-photonic, particle types of radiation all have mass and energy, they can be related to one another by their linear energy transfer (LET), which describes how much energy an ionizing particle transfers to material that it traverses, per unit distance.

Alpha radiation consists of ejected helium nuclei, which are heavy, very short-range particles containing two protons and two neutrons. Most alpha radiation is not able to penetrate human skin, although alpha-emitting materials can be harmful to humans if inhaled, swallowed, or absorbed through open wounds. Examples of alpha emitters include radium, radon, uranium, and thorium.

Beta radiation consists of ejected electrons or positrons, which are light, short-range particles that may travel several feet in air. Beta radiation has the ability to penetrate human skin to the "germinal layer" at which new skin cells are produced. Beta-emitting materials that are allowed to remain on the skin for a prolonged period of time may cause skin injury, and may be harmful if deposited internally. Examples of beta emitters include strontium-90, carbon-14, tritium, and sulfur-35. Neutron radiation consists of free neutrons released from atoms as a result of nuclear fission or nuclear fusion. Free neutrons have no charge, but can react with nuclei of other atoms to form new isotopes, which, in turn, can produce radiation.

Proton radiation can be generated using a particle accelerator to produce a beam of protons. Protons have a relatively large mass, and all protons of a given energy have a certain range of penetration into tissue. Because of this feature, proton radiation can be useful for highly targeted treatment of tumors. Proton radiation also is a significant component of the ionizing radiation produced by the sun.

HZE radiation consists of atomic nuclei with an atomic mass greater than helium that have no orbiting electrons, and thus have a charge of greater than +2. They can be generated by large particle accelerators, and are only found in nature as a component of galactic cosmic radiation, presumed to be generated mainly by supernovas beyond Earth's solar system. Common HZE ions include $C^{+6}$, $O^{+8}$, and $Fe^{+26}$. The frequency of HZE nucleons is inversely proportional to their atomic number, but the relative biological effect scales with increasing atomic number. For example, while $Fe^{+26}$ may only makeup 1% of galactic cosmic radiation, it could account for up to 50% of the biological damage from exposure to such radiation.

Radiation in nature typically is encountered as a mixed field (MF) that contains multiple types of radiation, rather than as a single beam exposure of the type commonly created by man. MF radiation can include various combinations of proton radiation, neutron radiation, alpha and/or beta radiation, and photon radiation. For example, in the event of an unshielded nuclear fission event (e.g., an attack or a reactor meltdown), individuals would likely be exposed to a miasma of photons, neutrons, alpha, and beta particles.

The physical differences between various types of ionizing radiation underlie their respective toxicities. For example, when gamma radiation passes through a cell, much of the resulting damage is mediated indirectly via oxidation of water, rather than through direct ionization of biological material. When charged particle radiation contacts a cell, not only is there an oxidative component to the toxicity, but secondary events also can occur as the radiation particles pass through the cellular material. These secondary ionizations (delta rays) occur when electrons are displaced by the primary radiation beam and travel perpendicularly to the primary axis of the ray until they are absorbed. The frequency of delta ray production is dependent on the LET. The more delta rays that are produced, the more localized damage occurs along the track of the primary particle. Thus, secondary ionization events can cause highly localized complex damage to biological material, and can surpass the oxidative component of the toxicity. Thus, equivalent doses of different forms of radiation can have dramatically different biological consequences. The varying consequences of different forms of radiation can be described by Relative Biological Effect (RBE), which serves simply as a multiplier to relate one form to another.

As different forms of ionizing radiation are differentially toxic to human biology, so too are there different therapeutic modalities for treating or preventing such toxicities. For example, some radiation countermeasures are free-radical scavengers, which can detoxify radiation exposure by limiting oxidative damage. While this may be an avenue for treatment of photon radiation exposure, the complex biological damage resulting from, for example, HZE radiation limits the effectiveness of countermeasures that possess antioxidant activity. Thus, the efficacy of a countermeasure against some forms of ionizing radiation does not predict its efficacy against all forms of ionizing radiation.

Because of radiation's ionizing effects on cells, exposure to radiation can have detrimental consequences, posing health risks to exposed individuals. The risks of terrestrial exposure to ionizing radiation include, for example, ARS, and DEARE, such as carcinogenesis, damage to the central nervous system, and degenerative effects on tissue, such as fibrosis. Ionizing radiation encountered during space missions also can present potential health problems for astronauts, with a significant risk of ARS (Wu et al., "Risk of Acute Radiation Syndromes Due to Solar Particle Events." In: McPhee and Charles (Eds.), *Human Health and Performance Risks of Space Exploration Missions*, NASA, pp. 171-190, 2009). Radiation exposure from the space environment also may increase the risk of cancer morbidity or mortality risk in astronauts (Cucinotta and Durante, "Risk of Radiation Carcinogenesis." In: McPhee and Charles (Eds.), *Human Health and Performance Risks of Space Exploration Missions*, NASA, pp. 119-170, 2009). The most likely ARS effects from SPE exposure in space flight, which could affect mission success, include prodromal effects (nausea, vomiting, anorexia, and fatigue), skin injury, and depletion of blood-forming organs. SPEs are of lower energy than are GCRs, and shielding typically is an effective countermeasure to SPEs inside spacecraft. Exposure is likely to be higher during extravehicular activity, however, and the magnitude of ARS risks may be increased due to factors such as background GCR exposure (Wu et al., supra).

Given the health risks of ionizing radiation, it is important to mitigate the effects of exposure in subjects who have been exposed to, or are at risk of exposure to, ionizing radiation. Those who are most likely to be exposed to ionizing radiation include, for example, cancer patients treated with radiation therapy (e.g., gamma radiation or proton radiation), workers in nuclear power plants, military personnel, and first responders to nuclear incidents (e.g., medical personnel and hazmat teams). Another group of individuals who may encounter ionizing radiation includes astronauts, since ionizing radiation exists in outer space. During space travel, astronauts are exposed to various types of radiation, including galactic cosmic rays (GCR) that are composed of proton radiation and charged HZE nuclei, and solar particle events that mostly consist of proton radiation protons (Sridharan et al., *Radiation Res* 183:1-26, 2015) but may also include other types of radiation. GCRs can be difficult to shield against, given their high energies. SPEs, which are produced in the solar corona and are associated with flares, can be difficult to predict beyond a matter of hours in advance, and can last for hours or even days (Hassler et al., *Science* 343(6169), DOI: 10.1126/science.1244797, 2014). It is thought that every cell nucleus within an astronaut traveling to Mars would be traversed by a proton or secondary electron every few days, and by an HZE ion every few months (Cucinotta et al., *Radiat Meas* 31:181-191, 1998).

As described herein, compositions containing genistein can be used as medical countermeasures that can reduce or prevent detrimental effects of exposure to ionizing radiation, and in some cases, can increase survival after such exposure. Genistein (5,7-dihydroxy-3-(4-hydroxyphenyl)-chromen-4-one (IUPAC), 5,7-dihydroxy-3-(4-hydroxyphenyl)-4H-1-benzopyran-4-one, 5,7,4'-trihydroxyisoflavone, 4',5,7-trihydroxyisoflavone) is a phytoestrogen in the category of isoflavones. Its chemical structure is shown in Formula (1):

Formula (1)

Genistein is one of several known isoflavones that are normally found in plants. The main sources of natural genistein are soybeans and other legumes. Genistein also is commercially available, and may be obtained in synthetic, purified form (e.g., from DSM Nutritional Products, Inc., Parsippany, N.J.).

Figure 1:
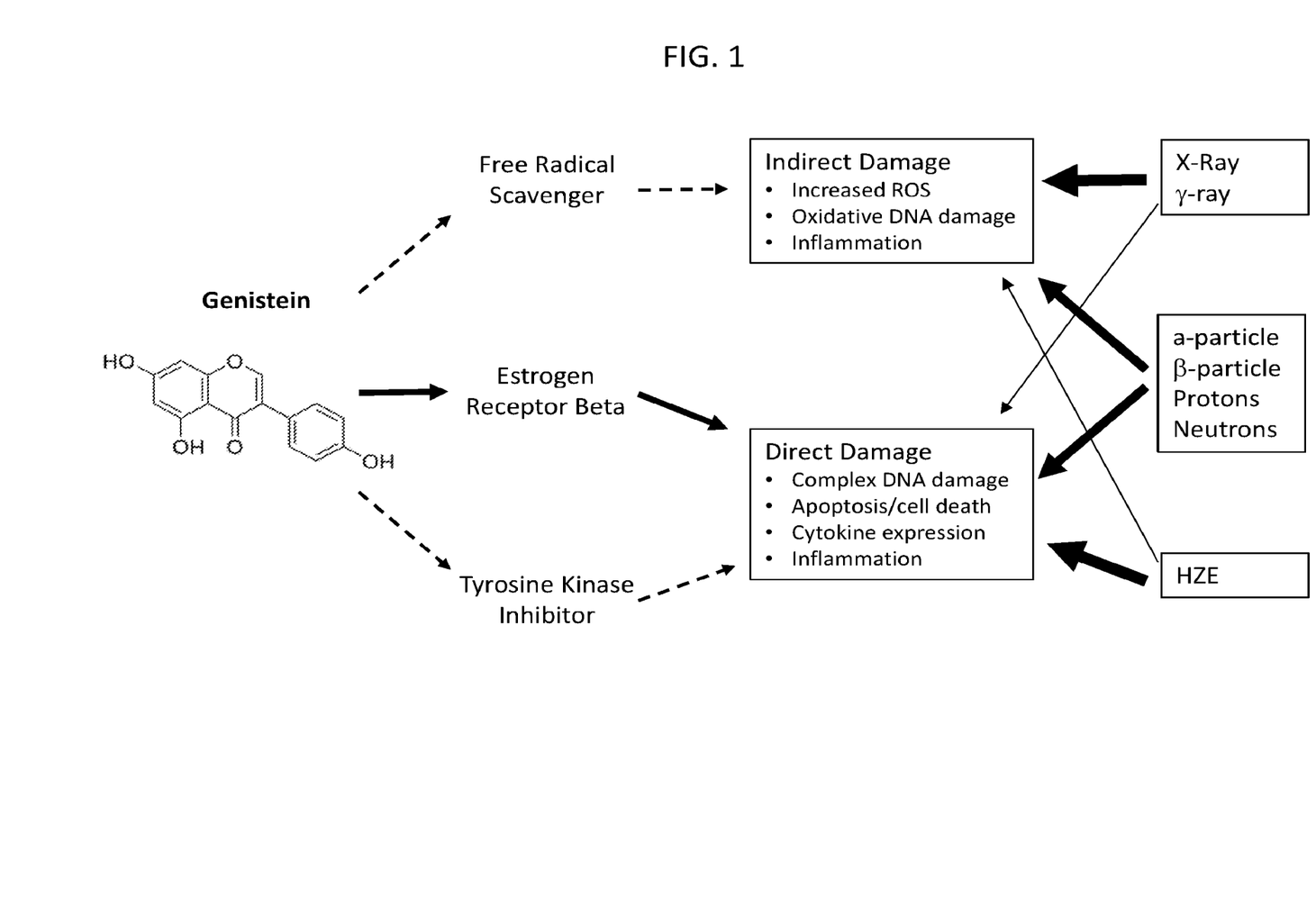

Genistein's radioprotective properties may be mediated, at least in part, by its activity as a selective agonist of estrogen receptor beta (ERβ). ERβ activation can inhibit cell proliferation via upregulation of its target genes, which encode cellular checkpoint and damage repair proteins. Other pharmacological properties of genistein that may mediate radioprotection include tyrosine kinase inhibition and free-radical scavenging, as depicted in FIG. 1.

As described herein, a formulation of genistein that can be distinguished from other radioprotectants and sources of genistein can be used to mitigate toxicities from various sources of radiation, including proton radiation (e.g., high LET proton radiation). In some embodiments, a composition can include genistein nanoparticles, which can have improved oral and/or parenteral bioavailability as compared to genistein that is not in nanoparticle form. Nanoparticle formulations can contain sub-micron size genistein particles, which can be manufactured using a wet nanomilling process that reduces genistein to a median particle size of less than 0.2 μm. See, e.g., U.S. Pat. No. 8,551,530. Pharmacokinetic experiments using such a genistein nanosuspension in mice demonstrated dramatically increased oral bioavailability as compared to formulations containing non-micronized genistein. See, FIGS. 4-7 of U.S. Pat. No. 8,551,530.

In some cases, the genistein compositions used in the methods provided herein can be formulations that include genistein in a solution containing one or more pharmaceutically acceptable carriers, excipients, and/or diluents. In some embodiments, the genistein compositions used in the methods provided herein can be suspension formulations that include nanoparticulate genistein suspended in a medium containing one or more pharmaceutically acceptable carriers, excipients, and/or diluents. Pharmaceutically acceptable carriers, excipients, and diluents suitable for therapeutic use include those described, for example, in *Remington's Pharmaceutical Sciences*, Maack Publishing Co. (A. R. Gennaro (ed.), 1985). In some cases, polyethylene glycol (PEG) can be used as a carrier in a composition that also contains genistein that is not in nanoparticle form.

In some embodiments, genistein compositions can include a suspension containing nanoparticulate genistein suspended in a non-aqueous medium, such as an edible plant or animal oil (e.g., olive oil, sunflower oil, corn oil, soy oil, marine oil, coconut oil, palm oil, palm kernel oil, cotton seed oil, safflower oil, sesame oil, peanut oil, almond oil, cashew oil, pecan oil, pine nut oil, macadamia oil, orange oil, flax seed oil, lemon oil, walnut oil, borage oils, fish oils, and dairy derived fats). See, e.g., U.S. Pat. No. 9,084,726.

Genistein compositions can, in some embodiments, include a suspension containing nanoparticulate genistein suspended in a medium including one or more water soluble polymers and one or more nonionic surfactants. See, e.g., U.S. Pat. No. 8,551,530.

Nonionic surfactants can facilitate wetting and aid in preventing agglomeration of the nanoparticulate genistein, for example. Suitable nonionic surfactants include, without limitation, polysorbates, poloxamers, polyoxyethylene castor oil derivatives, bile salts, lecithin, 12-hydroxystearic acid-polyethylene glycol copolymer, and the like. In some embodiments, a genistein composition can include a nonionic surfactant selected from the group consisting of polysorbate 80 (TWEEN® 80), polysorbate 20 (TWEEN® 20), Poloxamer 188, and combinations thereof. The total nonionic surfactant content in the genistein compositions provided herein can range from about 0.01% to about 10% by weight (w/w) (e.g., about 0.2% to about 5% (w/w), about 0.2% to about 2% (w/w), about 0.2% to about 1% (w/w), about 0.2% to about 0.6% (w/w), and about 0.2% to about 0.8% (w/w).

Water soluble polymers can serve to enhance the viscosity of a suspension and/or to stabilize nanoparticulate genistein against particle agglomeration or potential deleterious effects from other formulation components, for example. Water soluble polymers are pharmaceutically acceptable polymers that can be dissolved or dispersed in water. Suitable water soluble polymers include, without limitation, vegetable gums (e.g., alginates, pectin, guar gum, and xanthan gum), modified starches, polyvinylpyrrolidone (PVP), hypromellose (HPMC), methylcellulose, and other cellulose derivatives (e.g., sodium carboxymethylcellulose, hydroxypropylcellulose, and the like). In some embodiments, the genistein compositions described herein can include a poloxamer (e.g., Poloxamer 188) as a water soluble polymer. Poloxamer 188 is both a polymer and surfactant. The total water soluble polymer content in a genistein composition as provided herein can range from about 0.5% to about 15% (w/w) [e.g., about 1% to about 10% (w/w), about 10% to about 15% (w/w), about 12% to about 15% (w/w), about 1% to about 8% (w/w), and about 1% to about 5% (w/w)].

Carriers suitable for use in the genistein formulations described herein also include pharmaceutically acceptable aqueous carriers such as, sterile water, physiologically buffered saline, Hank's solution, and Ringer's solution. The formulations also can contain one or more buffers [e.g., one or more citrate buffers, phosphate buffers, tris(hydroxymethyl)aminomethane (TRIS) buffers, and/or borate buffers], to achieve a desired pH and osmolality. Injectable pharmaceutical formulations typically have a pH in the range of about 2 to about 12. In some embodiments, the genistein formulations provided herein can have a pH that falls in a range that more closely approximates physiologic pH (e.g., about 4 to about 8, or about 5 to about 7).

The genistein compositions provided herein also can include one or more diluents. Suitable diluents include those selected from, without limitation, pharmaceutically acceptable buffers, solvents, and surfactants.

In some embodiments, a genistein composition can include PVP (e.g., 5% PVP-K17) and polysorbate 80 (e.g., 0.2% polysorbate 80), as well as phosphate buffered saline (PBS, e.g., 50 nM PBS). In some cases, an oral formulation of a genistein composition can contain PVP (e.g., PVP-K25), polysorbate 80 (TWEEN® 80), and one or more preservatives (e.g., methyl paraben, propyl paraben, benzyl alcohol, or any combination thereof). In addition, a composition can include a diluent such as a sodium chloride solution. The particle size distribution of the genistein nanoparticulate composition can be $d(0.5) \leq 0.50$ microns (e.g., $d(0.5) \leq 0.40$ microns, $d(0.5) \leq 0.30$ microns, or $d(0.5) \leq 0.20$ microns). See, e.g., U.S. Pat. No. 8,551,530. It is to be noted that while such genistein formulations are characterized as suspensions, depending on the carriers, excipients, and diluents included in the suspension medium, a measurable amount of genistein also may be dissolved in the suspension medium.

Genistein exhibits low to virtually no solubility in several pharmaceutically acceptable solvents, but a nanoparticulate suspension of genistein as described herein can provide a high concentration of genistein. For example, a suspension of nanoparticulate genistein can incorporate genistein in amounts ranging from about 100 mg/mL to about 500 mg/mL (e.g., ranges from about 100 mg/mL to about 400 mg/mL, about 150 mg/mL to about 350 mg/mL, about 200 mg/mL to about 400 mg/mL, about 250 mg/mL to about 350 mg/mL, about 275 mg/mL to about 325 mg/mL, about 300 mg/mL to about 450 mg/mL, or about 350 mg/mL to about 500 mg/mL, or amounts of about 100 mg/mL, about 150 mg/mL, about 200 mg/mL, about 250 mg/mL, about 275 mg/mL, about 300 mg/mL, about 325 mg/mL, about 350 mg/mL, about 375 mg/mL, about 400 mg/mL, about 450 mg/mL, or about 500 mg/mL). The relative amount of genistein included in such a suspension can be varied to yield a formulation having a desired total content of genistein. For example, a suspension formulation as described herein can include up to about 50% (w/w) genistein [e.g., about 50% (w/w), about 45% (w/w), about 40% (w/w), about 35% (w/w), about 30% (w/w), about 25% (w/w), about 20% (w/w), about 15% (w/w), about 10% (w/w), about 40% to about 50% (w/w), about 35% to about 45%, about 30% to about 40% (w/w), about 25% to about 35% (w/w), about 20% to about 30% (w/w), about 20% to about 35% (w/w), about 15% to about 35%, about 10% to about 30%, or about 10% to about 25%]. In some embodiments, nanoparticle genistein suspensions can provide increased bioavailability of genistein as compared to the bioavailability of genistein provided by solution formulations (e.g., solutions containing a pharmaceutically acceptable PEG solvent or containing larger sized genistein material). As described in U.S. Pat. No. 8,551,530, for example, the combination of high genistein loading and significantly increased bioavailability can provide advantages, such as facilitating administration of therapeutically effective amounts of genistein using much lower amounts of formulated drug substance, for example.

Genistein compositions can be formulated for administration by any suitable method, depending upon whether local or systemic treatment is desired and upon the area to be treated. For example, a genistein composition can be formulated for oral administration, parenteral administration (e.g., by subcutaneous, intrathecal, intraventricular, intramuscular, or intraperitoneal injection, or by intravenous drip), pulmonary administration (e.g., by inhalation or insufflation of powders or aerosols or a nebulized mist), or by a combination of routes such as oral and parenteral administration. Administration can be rapid (e.g., by injection) or can occur over a period of time (e.g., by slow infusion or administration of slow release formulations, such as from subcutaneous drug depots, slow short term intravenous injections, or slow release oral formulations).

Compositions and formulations for parenteral administration include, for example, sterile solutions (e.g., sterile aqueous solutions or suspensions) that also can contain buffers, diluents, and/or other suitable additives (e.g., penetration enhancers, carrier compounds and other pharmaceutically acceptable carriers). Compositions formulated for parenteral delivery can be manufactured according to standard methods to provide sterile compositions deliverable via, for example, intravenous injection or infusion, intravascular injection, subcutaneous injection, or intramuscular injection. A genistein formulation (e.g., a suspension of nanoparticulate genistein) can be prepared to have a viscosity suitable for the desired route of parenteral administration, and can be manufactured and packaged in any manner suited to the desired application, including, without limitation, as a formulation deliverable via intravenous injection or infusion, intravascular injection, subcutaneous injection, or intramuscular injection. In some embodiments, a formulation as described herein can be contained in one or more pre-filled syringes or auto-injectors prepared for administration of a given dose or range of doses of genistein.

Genistein compositions also can be formulated for oral administration. Compositions and formulations for oral administration include, for example, powders or granules, suspensions or solutions in water or non-aqueous media (e.g., suspensions of genistein nanoparticles in edible oil), capsules, gel caps, sachets, and tablets. In some embodiments, a genistein composition can be prepared as a liquid suspension that can be metered to deliver a desired dose, or can be incorporated into capsules (e.g., gelatin or soft capsules) suitable for delivery of liquid formulations. Alternatively, formulations for oral administration can be loaded into prefilled sachets or premetered dosing cups. In some embodiments, such genistein formulations also can include one or more pharmaceutically acceptable sweetening agents, preservatives, dyestuffs, flavorings, or any combination thereof.

Genistein compositions useful in the methods described herein can further include any pharmaceutically acceptable genistein salts, esters, or salts of such esters, or any other genistein compound which, upon administration to an animal such as a human, is capable of providing (directly or indirectly) biologically active genistein or an active metabolite or residue thereof. Accordingly, for example, provided herein are pharmaceutically acceptable salts of genistein, prodrugs and pharmaceutically acceptable salts of such prodrugs, and other bioequivalents. The term "prodrug" indicates a therapeutic agent that is prepared in an inactive form and is converted to an active form (i.e., drug) within the body or cells thereof by the action of endogenous enzymes or other chemicals and/or conditions. The term "pharmaceutically acceptable salts" refers to physiologically and pharmaceutically acceptable salts of genistein (e.g., salts that retain the desired biological activity of genistein without imparting undesired toxicological effects). Examples of pharmaceutically acceptable salts may include, for example, salts formed with cations (e.g., sodium, potassium, calcium, or polyamines such as spermine), acid addition salts formed with inorganic acids (e.g., hydrochloric acid, hydrobromic acid, sulfuric acid, phosphoric acid, or nitric acid), and salts formed with organic acids (e.g., glucuronic acid, acetic acid, citric acid, oxalic acid, palmitic acid, or fumaric acid). Depending on the route of administration, for example, genistein may be sulfated or in glucuronic acid form.

Compositions also can include other adjunct components conventionally found in pharmaceutical compositions. Thus, the compositions also can include compatible, pharmaceutically active materials such as, for example, antipruritics, astringents, local anesthetics or anti-inflammatory agents, or additional materials useful in physically formulating various dosage forms of the compositions provided herein, such as dyes, flavoring agents, preservatives, antioxidants, opacifiers, thickening agents and stabilizers. Furthermore, the composition can be mixed with auxiliary agents, e.g., lubricants, preservatives, stabilizers, wetting agents, emulsifiers, salts for influencing osmotic pressure, buffers, colorings, flavorings, and aromatic substances. When added, however, such materials should not unduly interfere with the biological activities of the genistein within the composition. The formulations can be sterilized if desired.

This document also provides methods for using genistein compositions as countermeasures against the effects of ionizing radiation. Such countermeasures can be used to prevent, reduce, or mitigate effects such as carcinogenesis, damage to the central nervous system, degenerative effects on tissue, and even death.

In some embodiments, for example, this document provides methods for treating a subject to prevent, reduce, or mitigate one or more effects of potential exposure to ionizing radiation. The methods can include identifying a subject as being at risk for exposure to ionizing radiation, and administering to the subject an effective dose of a genistein-containing composition. The subject can be, for example, a human or a non-human mammal. Subjects at risk for exposure to ionizing radiation may be individuals who will undergo radiation therapy (e.g., proton therapy) for cancer, individuals present or likely to be present in an industrial or military setting in which exposure to ionizing radiation could occur, or astronauts. In some cases, such individuals can be treated with a genistein-containing composition prophylactically, before exposure to ionizing radiation has occurred. In some embodiments, an individual can be treated on a daily or weekly basis (e.g., every day, about six days per week, about five days per week, about four days per week, about three days per week, or about two days per week), before potential exposure to ionizing radiation. In some embodiments, an individual can be treated within about 1 hour to about 6 days (e.g., within about 5 to 6 days, about 4 to 5 days, about 3 to 4 days, about 60 to 72 hours, about 48 to 60 hours, about 36 to 48 hours, about 24 to 36 hours, about 18 to 24 hours, about 12 to 18 hours, about 10 to 12 hours, about 8 to 10 hours, about 6 to 8 hours, about 4 to 6 hours, about 2 to 4 hours, or about 1 to 2 hours) before potential exposure, such as before entering an area of increased risk for exposure to ionizing radiation or before an imminent SPE event, to prevent or reduce potential harmful effects, should such exposure occur.

In some embodiments, this document provides methods for treating a subject to reduce, prevent, or mitigate one or more effects of exposure to ionizing radiation. The methods can include identifying a subject as having been exposed to ionizing radiation (e.g., exposed once, exposed more than once, such as for fractionated proton radiation therapy for cancer treatment, or exposed continuously over a period of time), and administering to the subject an effective dose of a genistein-containing composition. In some embodiments, the subject can be a human or a non-human mammal, and can be an individual exposed to ionizing radiation in a medical setting (e.g., a cancer patient treated with proton radiation therapy) or in an industrial or military setting, or in outer space. Such subjects can be treated on an hourly, daily, or weekly basis after exposure, in order to mitigate harmful effects of exposure to the ionizing radiation. In some embodiments, the genistein composition can be administered within about four weeks or less (e.g., within about three weeks, two weeks, or one week), or within about 96 hours or less (e.g., within about 72 to 96 hours, about 48 to 72 hours, about 24 to 48 hours, about 20 to 24 hours, about 18 to 20 hours, about 16 to 18 hours, about 12 to 16 hours, about 8 to 12 hours, about 6 to 8 hours, about 4 to 6 hours, or about 2 to 4 hours), or within about 60 minutes or less (e.g., within about 45 to 60 minutes, about 30 to 45 minutes, about 15 to 30 minutes, about 10 to 15 minutes, or about 5 to 10 minutes) after exposure. Administration can continue on an hourly, daily, weekly, or monthly basis to mitigate the effects of exposure to the ionizing radiation. For example, a genistein-containing composition can be administered one or more times daily, every other day, biweekly, weekly, bimonthly, monthly, or less often, for any suitable length of time after exposure to the radiation has occurred (e.g., for about a week, about two weeks, about three weeks, about a month, about six weeks, about two months, about three months, about six months, about a year, or more than a year after exposure).

The methods provided herein include administering to a subject a composition that contains genistein in any formulation suitable to deliver an effective dose of genistein to the subject, where the dose is effective to prevent, reduce, or mitigate effects of the ionizing radiation to which the subject has been or may be exposed. As used herein, a dose administered that is "effective to reduce" the effects of the radiation is a dose that is sufficient to decrease one or more effects of exposure (should such exposure occur) by at least ten percent (e.g., at least ten percent, at least 25 percent, at least 50 percent, or at least 75 percent) as compared to the level of the effects in a corresponding subject to which the composition was not administered. In some embodiments, an effective dose can prevent development of one or more effects of exposure to the ionizing radiation. As used herein, a dose administered that is "effective to mitigate" the effects of ionizing radiation is a dose that is sufficient to reduce the effects of exposure by at least ten percent (e.g., at least ten percent, at least 25 percent, at least 50 percent, or at least 75 percent), as compared to a corresponding subject to which the composition was not administered. Effective doses (e.g., therapeutically or prophylactically effective doses) can be effective to prevent, reduce, or mitigate effects of exposure to ionizing radiation that include, without limitation, ARS effects, carcinogenesis, central nervous system damage, degenerative effects on tissue, and death.

In some embodiments, a composition can contain genistein (e.g., nanoparticulate genistein or genistein that is not in nanoparticle form), at a concentration between about 100 mg/mL and about 500 mg/mL (e.g., about 100 mg/mL to about 400 mg/mL, about 150 mg/mL to about 350 mg/mL, about 200 mg/mL to about 400 mg/mL, about 250 mg/mL to about 350 mg/mL, about 275 mg/mL to about 325 mg/mL, about 300 mg/mL to about 450 mg/mL, or about 350 mg/mL to about 500 mg/mL). Compositions containing nanoparticulate genistein can have a particle size distribution characterized by a median diameter [d(0.5)] that is less than or equal to 0.5 μm (e.g., less than or equal to 0.4 μm, less than or equal to 0.3 μm, or less than or equal to 0.2 μm). The composition also can contain one or more other components, as described herein (e.g., one or more pharmaceutically acceptable excipients that form a suspension medium, such as a water soluble polymer, a nonionic surfactant, a diluent, or a buffer). In some embodiments, the suspension medium may be non-aqueous, such as edible lipids, oils, and fats from plant and animal sources (e.g., olive, corn, soy, marine, coconut, palm, palm kernel, cotton seed, peanut, safflower, sesame, sunflower, almond, cashew, macadamia, pecan, pine nut, walnut, lemon, orange, flax seed, and borage oils).

The administering step can be accomplished via any suitable route. In some embodiments, for example, a genistein composition containing a solution of genistein or a suspension of genistein nanoparticles can be administered orally or parenterally (e.g., by injection, such as subcutaneous, intravenous, or intramuscular injection).

In some embodiments, a prophylactic or therapeutic dose of a genistein-containing composition can contain about 0.25 g to about 2.5 g of genistein (e.g., about 0.25 g to about 0.3 g, about 0.3 g to about 0.4 g, about 0.4 g to about 0.5 g, about 0.5 g to about 0.75 g, about 0.75 g to about 1 g, about 1 g to about 1.25 g, about 1.25 g to about 1.5 g, about 1.5 g to about 1.75 g, about 1.75 g to about 2 g, about 2 g to about 2.25 g, or about 2.25 g to about 2.5 g). In some cases, a dose of a genistein-containing composition can be effective to achieve a blood concentration of aglycone (unconjugated, non-glucuronidated) genistein of about 0.35 μM to about 5 μM (e.g., about 0.5 μM, about 1 μM, about 1.5 μM, about 2 μM, about 3 μM, about 4 μM, about 5 μM, about 0.35 to about 0.5 μM, about 0.5 to about 0.75 μM, about 0.75 to about 1 μM, about 0.75 to about 1.25 μM, about 1 to 1.5 μM, about 1.5 to 2.5 μM, or about 2.5 to 5 μM).

In some embodiments, a genistein composition can be administered to a subject at a dose of about 5 mg/kg to about 500 mg/kg (e.g., about 5 to 10 mg/kg, about 10 to 25 mg/kg, about 25 to 50 mg/kg, about 50 mg/kg, about 75 to 100 mg/kg, about 100 to 200 mg/kg, about 200 to 300 mg/kg, about 300 to 400 mg/kg, or about 400 to 500 mg/kg). The dose can be administered on a daily to weekly to monthly basis or longer (e.g., for about 1 day to about 2 years, such as from 1 to 3 days, 3 to 7 days, 7 to 10 days, 10 to 14 days, 14 to 21 days, 21 to 28 days, 28 to 35 days, 30 to 45 days, 45 to 60 days, two to three months, three to six months, six to nine months, nine months to a year, one to 1.5 years, 1.5 to 2 years, or more than 2 years).

In some embodiments, a therapeutic method can include administering a first dose of genistein for a first period of time after exposure to ionizing radiation, and then administering a second dose of genistein for a second period of time. The first dose can be higher than the second dose. For example, a method can include administering a genistein-containing composition at a dose of 0.25 g to about 2.5 g per day (e.g., about 0.25 g to about 0.3 g, about 0.3 g to about 0.4 g, about 0.4 g to about 0.5 g, about 0.5 g to about 0.75 g, about 0.75 g to about 1 g, about 1 g to about 1.25 g, about 1.25 g to about 1.5 g, about 1.5 g to about 1.75 g, about 1.75 g to about 2 g, about 2 g to about 2.25 g, or about 2.25 g to about 2.5 g per day) for about 1 day to about 6 months (e.g., about 1 day to about 3 days, about 3 days to about 7 days, about 7 days to about 2 years, such as from 7 to 10 days, 10 to 14 days, 14 to 21 days, 21 to 28 days, 28 to 35 days, 30 to 45 days, 45 to 60 days, two to three months, or three to six months), and then administering the composition at a dose of about 0.1 g to about 1 g per day (e.g., about 0.1 g to about 0.7 g, 0.2 g to about 0.5 g, about 0.3 g to about 1 g, about 0.5 g to about 0.8 g, or about 0.5 g to about 1 g) for about 1 day to about 2 years (e.g., from 1 to 3 days, 3 to 7 days, 7 to 10 days, 10 to 14 days, 14 to 21 days, 21 to 28 days, 28 to 35 days, 30 to 45 days, 45 to 60 days, two to three months, three to six months, six to nine months, nine months to a year, one to 1.5 years, or 1.5 to 2 years).

This document also provides for the use of genistein compositions as described herein for preventing, reducing, or mitigating one or more effects of exposure to proton radiation in a subject identified as having been exposed to proton radiation or as being at risk of exposure to proton radiation. In addition, this document provides for the use of genistein in the manufacture of medicaments for preventing, reducing, or mitigating one or more effects of exposure to proton radiation in a subject identified as having been exposed to proton radiation or as being at risk of exposure to proton radiation.

Genistein formulations (e.g., genistein solutions or nanoparticle suspensions) can be combined with packaging material and sold as kits for preventing, reducing, or mitigating the effects of exposure to ionizing radiation. Thus, this document also provides articles of manufacture that can include one or more genistein-containing compositions. The articles of manufacture can further include, for example, buffers or other control reagents for reducing, preventing, or monitoring the effects of exposure to ionizing radiation. Instructions describing how genistein formulations are effective for preventing, reducing, or mitigating damage from such exposure also can be included in such kits.

In some embodiments, an article of manufacture can include a genistein formulation (e.g., a suspension of nanoparticulate genistein) contained within a means for administration, such as an auto-injector. For example, an auto-injector can contain a suspension of nanoparticulate genistein at a concentration between about 250 mg/mL and about 500 mg/mL, where the genistein nanoparticulate composition has a particle size distribution characterized by a d(0.5) of 0.5 μm or less (e.g., 0.4 μm or less, 0.3 μm or less, or 0.2 μm or less). The genistein composition also can include other components (e.g., one or more pharmaceutically acceptable excipients), as described herein.

Components and methods for producing articles of manufacture include those known in the art, for example. In addition, in some embodiments, pre-made auto-injectors can be obtained commercially, filled with a genistein nanoparticulate composition, and packaged as a kit for preventing, reducing, or mitigating the effects of exposure to ionizing radiation.

The invention will be further described in the following examples, which do not limit the scope of the invention described in the claims.

EXAMPLES

Example 1—Protective Effect of Genistein Against Proton Irradiation

Figure 2:
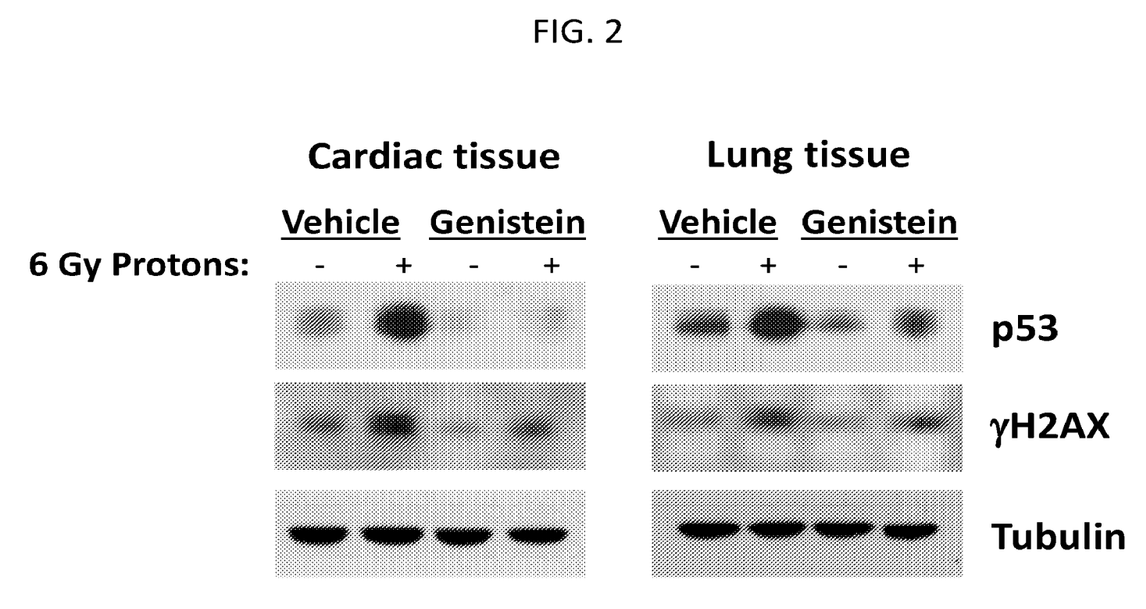
FIG. 2 is a western blot with heart and lung tissue extracted from animals that were treated with or without genistein [200 mg/kg subcutaneously (s.c.)] and then exposed to 6 Gy high LET proton radiation 24 hours after treatment. The indicated tissues were harvested 3 days later. The levels of p53 (a DNA damage response protein) and γH2AX (a direct measurement of DNA damage) were measured and compared to a tubulin control. In both tissues, genistein treatment prevented a marked increase in p53 levels in response to the radiation exposure. Genistein treatment also was correlated with lower levels of γH2AX. These results implied that genistein mitigates the toxicity from proton radiation.
Figure 3A:
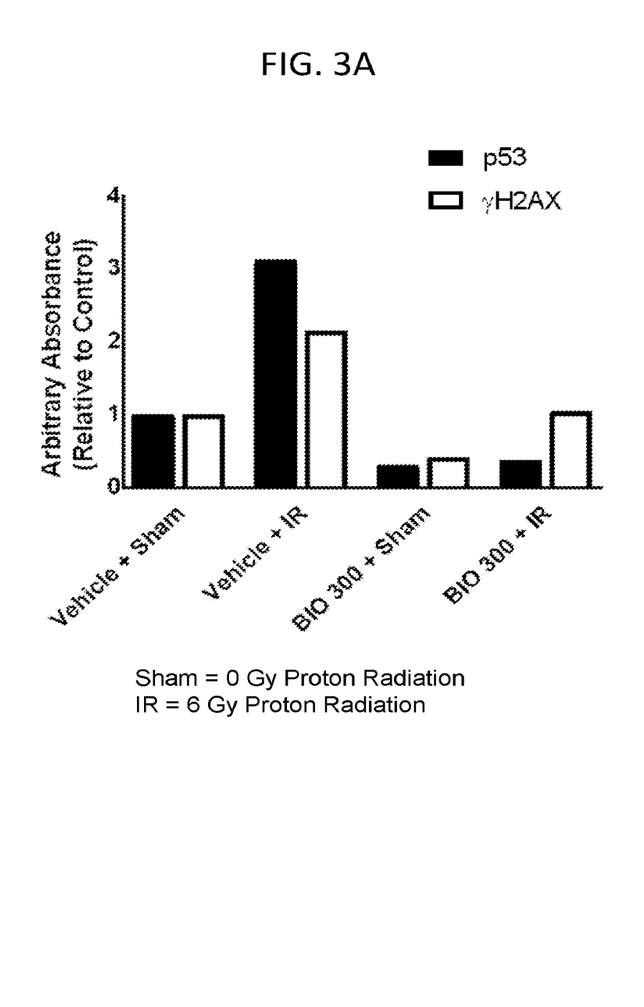
FIG. 3A is a graph plotting quantification of the western blot data for heart tissue as shown in FIG. 2.
Figure 3B:
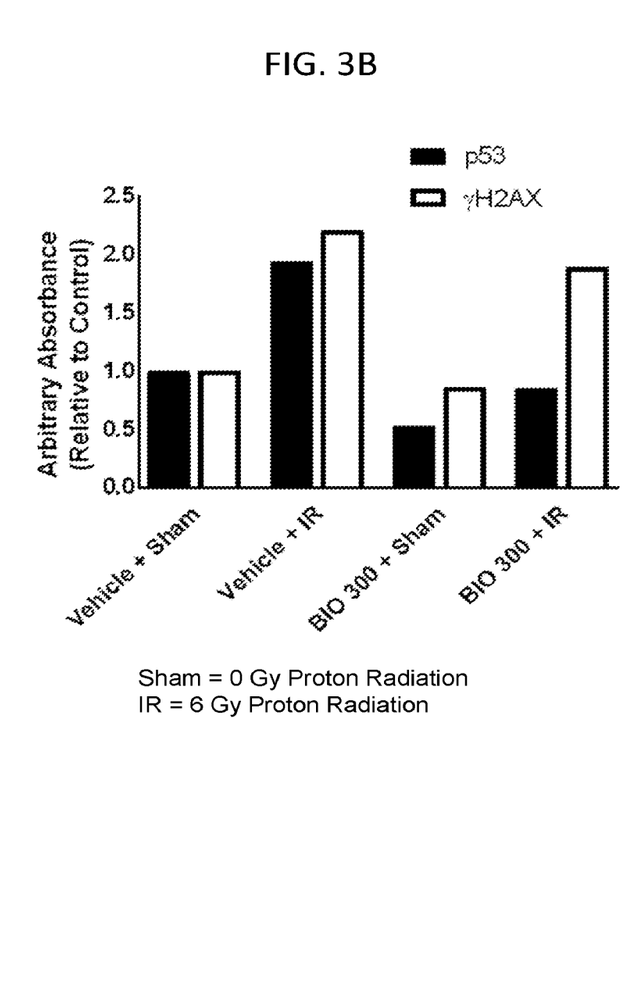
FIG. 3B is a graph plotting quantification of the western blot data for lung tissue as shown in FIG. 2.

Mice were prophylactically administered genistein (200 mg/kg) via s.c. injection 24 hours prior to radiation exposure. Appropriate sham radiation and vehicle controls were applied. Radiation exposures of 6 Gy with high-LET protons [50 MeV fully modulated spread-out Bragg peak (SOBP)] were utilized. The following parameters were examined:

DNA damage in tissues—Lungs and heart were surgically removed and subjected to thin-slice sectioning, followed by western blot analysis for the DNA damage markers p53 and γH2AX (an effective measure of proton radiation-induced biological damage; see, Liu et al., *Radiation Oncology* 91(5):1081-1089, 2015), as well as tubulin control. Genistein ameliorated the effects of proton radiation on expression of these markers (FIGS. 2, 3A, and 3B), indicating its ability to mitigate the toxicity of proton radiation.

Figure 4A:
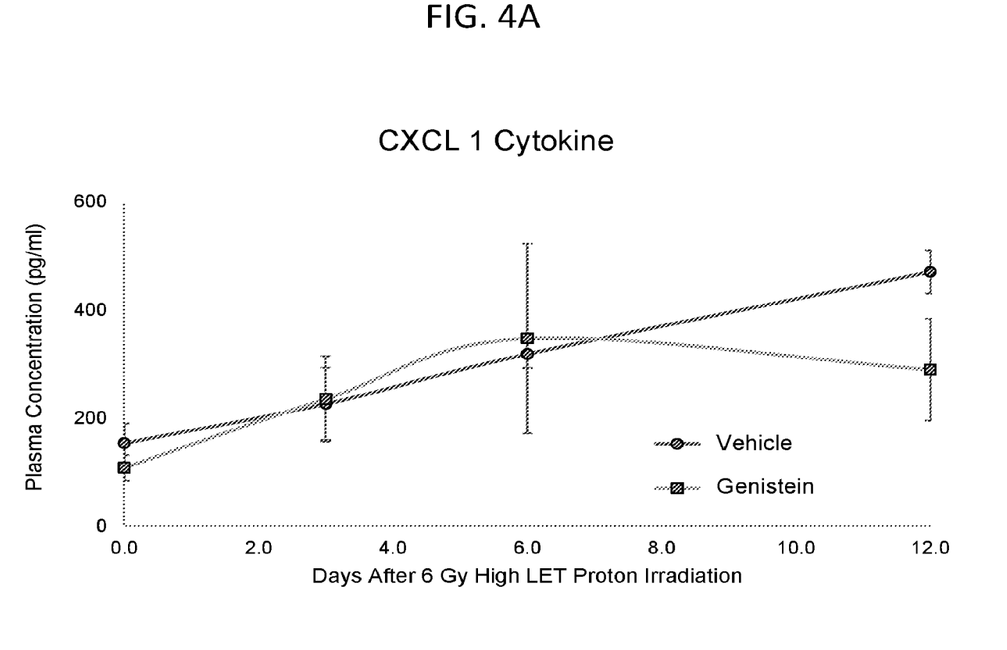
Figure 4B:
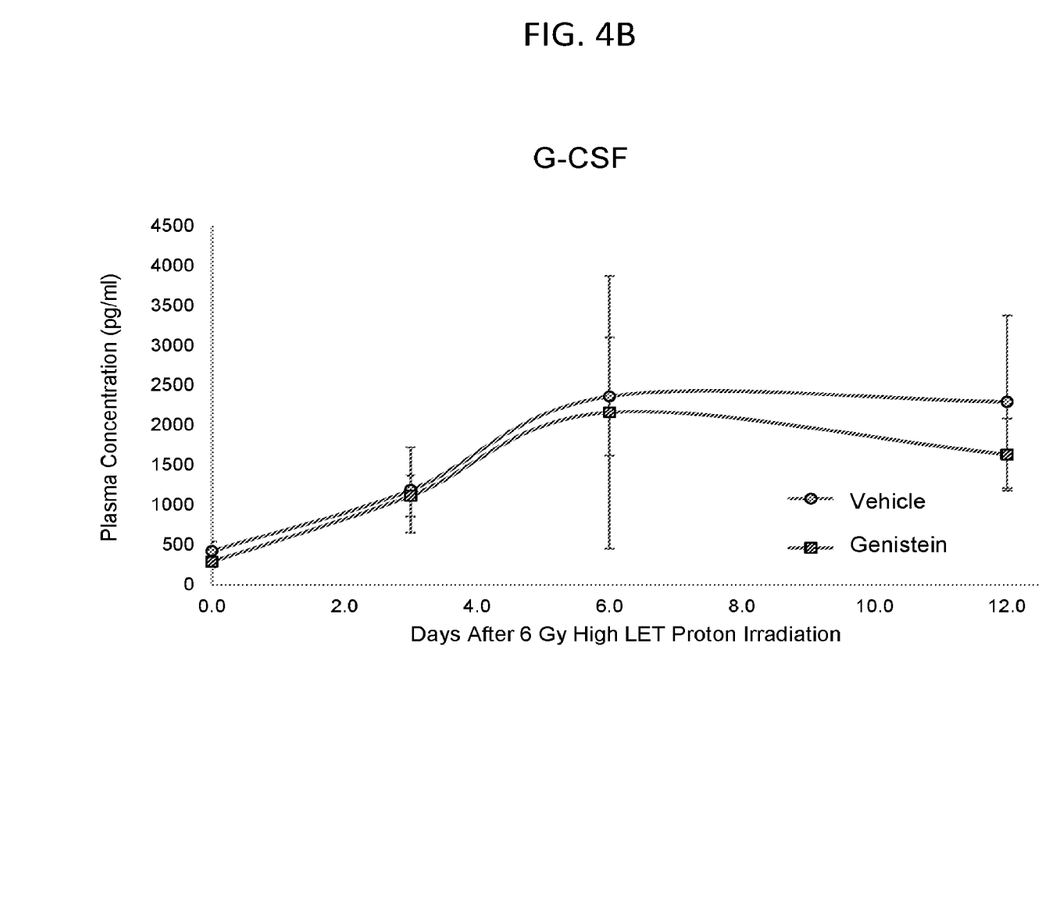
Figure 4C:
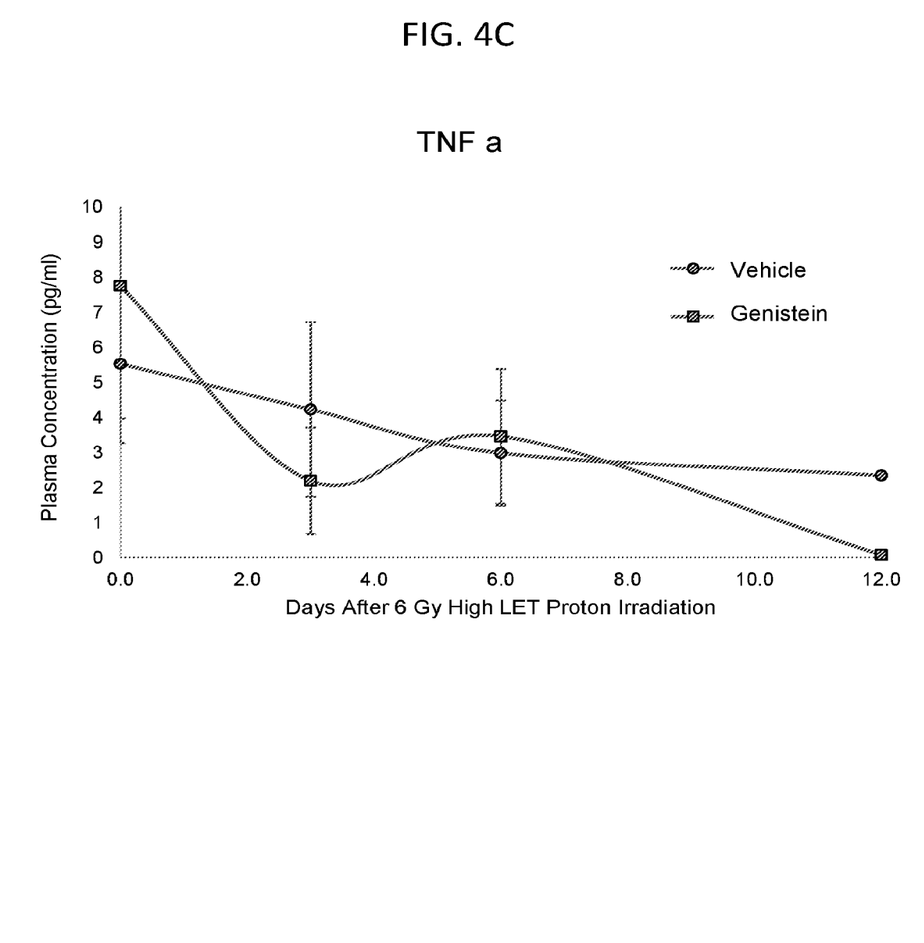

Cytokine response—Peripheral blood was taken from the treated and irradiated mice 3, 6, and 12 days after radiation exposure, and assessed using a multi-cytokine LUMINEX® panel to evaluate the global inflammatory cytokine response. As shown in FIGS. 4A, 4B, and 4C, specific cytokine responses were reduced by genistein treatment. In particular genistein mitigated the effects of proton radiation on expression of CXCL1 cytokine (FIG. 4A), G-CSF (FIG. 4B), and TNFα (FIG. 4C).

Example 2—Protective Effect of Genistein Against Mixed Field Radiation

Figure 5:
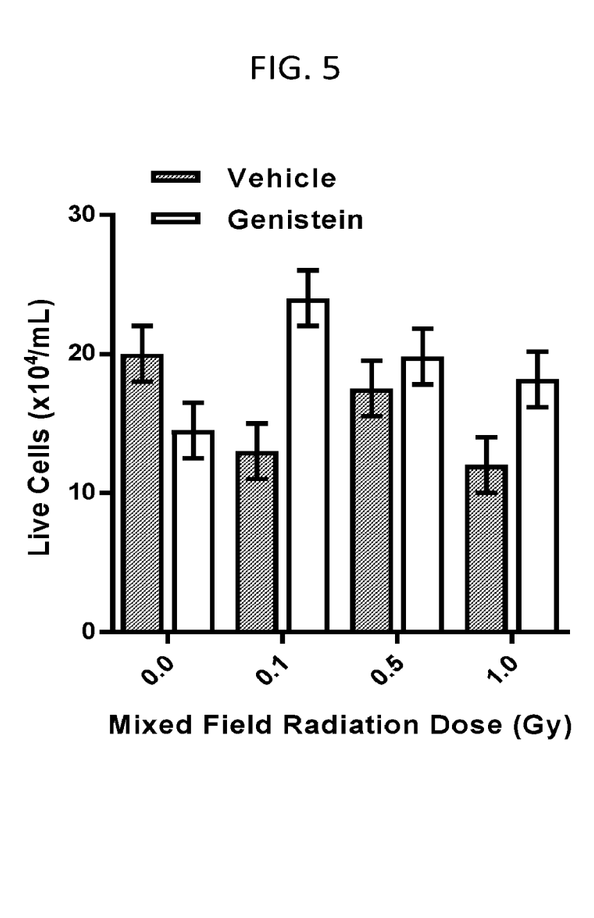
FIG. 5 is a graph plotting the number of live human cardiomyocytes after treatment of the cells with genistein 24 hours before exposure to various doses of mixed field (32% neutron, 68% gamma) radiation (henceforth referred to as "MF" radiation). Live cell counts were performed 3 days after radiation exposure. The genistein-treated cells exhibited increased survival after exposure to multiple doses of MF radiation. These data imply that genistein treatment can mitigate damage from MF radiation that includes particle radiation.

Human cardiomyocytes were treated with genistein 24 hours before exposure to various doses of mixed field ("MF," 32% neutron, 68% gamma) radiation. Live cell counts were performed 3 days after radiation exposure. The genistein-treated cells exhibited increased survival after exposure to multiple doses of MF radiation (FIG. 5). These data imply that genistein treatment can mitigate damage from MF radiation that includes particle radiation, and indicate that genistein is consistent in its radioprotective effects.

Example 3—Mitigation of the Incidence of Radiation-Induced Cancers

A cancer-prone genetic mouse model is utilized to determine if oral administration of 200 mg/kg genistein prevents an increased incidence in radiation-induced cancer after exposure to simulated space radiation. The space radiation simulations include various single ion beams, and mixed fields therein, which are produced at Brookhaven National Laboratory to simulate various spectra of space radiation. Readouts include the incidence of cancers of various tissues in each animal, overall survival, and lifespan.

Example 4—Prevention of Radiation-Induced Cognitive Dysfunction

Cognitive defects from ionizing radiation are known to result in humans undergoing radiotherapy for brain tumors. To determine whether genistein can reduce the occurrence of such defects, subjects likely to be exposed to various spectra of ionizing radiation are treated with oral genistein at a dose sufficient to achieve a blood concentration of aglycone (unconjugated, non-glucuronidated) genistein of about 1 µM. Consumption of genistein can be beneficial to mitigating such cognitive toxicity if it is consumed before, during, and/or after radiation exposure. Radiation exposure could range from clinical proton therapy in cancer patients to GCR exposure in space-travelling astronauts. The protective capacity of genistein on cognitive function is tested using standard cognitive tests.

The protective effects of genistein oral administration also are tested in nonclinical animals models (e.g., mice). Genistein (200 to 400 mg/kg) is orally administered to mice up to 7 days before radiation exposure, and possibly continuing for up to about 6 weeks after radiation exposure. At specific time intervals following radiation exposure and administration of genistein, the animals are subjected to validated cognitive function tests, such as the "Delayed, Non-Matching to Place Task," or the "Conditioned Eyeblink Reflex," as well as brain histopathological analyses to be conducted at necropsy of the test subject.

Example 5—Determining Whether a Genistein Composition Affects Radiation Toxicity in Mice Exposed to Protons with Increasing LET Further studies are conducted to evaluate genistein's in vivo protective effect against proton radiation when administered prophylactically. Mice are prophylactically orally gavaged with a daily dose of 400 mg/kg genistein, starting one to six days prior to radiation exposure. The prophylactic dose regimen consists of either a single daily dose of 400 mg/kg, or two daily doses of 200 mg/kg each. Appropriate sham radiation and vehicle controls are applied. The mice are sacrificed for analysis either 4 hours or 16 days after radiation treatment, and assessed for the parameters listed below. Study groups include five mice per condition, with two time points and two dosing schemes, requiring 30 animals/experiment. Initial studies include irradiating the mice at 6 Gy with high-LET protons (50 MeV fully modulated spread-out Bragg peak (SOBP)), and subsequent experiments are conducted with 4, 2, and 0.5 Gy doses in an effort to determine any threshold of radiation-exposure efficacy.

The in vivo studies include analysis of any or all of the following parameters.

1. Hematopoietic blood cell count. Complete blood cell (CBC) counts (WBC, ANC, and platelets) are determined 16 days post radiation exposure in the genistein-treated and untreated groups. This time point corresponds to the nadir in irradiated animals and thus provides a critical time point to evaluate genistein's efficacy.

2. Cytokine response. Peripheral blood is taken from the animals and assessed using a multi-cytokine LUMINEX® panel to assess the global inflammatory cytokine response. Peripheral blood is collected for cytokine analysis 4 hours and 16 days post radiation exposure.

3. DNA damage in tissues. Lungs, liver, and bowel from sacrificed animals (4 hours and 16 days post radiation exposure) are surgically removed and subjected to thin-slice sectioning, followed by immunohistological analysis for γH2AX, which has been demonstrated to be an effective measure of proton radiation-induced biological damage (Liu et al., *Radiation Oncology* 91(5):1081-1089, 2015). Additionally, pathological parameters such as fibrosis and evidence of inflammation are qualitatively assessed. Tissue analysis is performed on sections from groups of animals demonstrating therapeutic efficacy by CBC measures.

4. DNA damage markers in white blood cells. Peripheral blood is collected at 4 hours and 16 days post radiation exposure. White blood cells are purified and assessed for DNA damage markers, such as p53 and γH2AX, which are detected by FACS or western blot.

OTHER EMBODIMENTS

It is to be understood that while the invention has been described in conjunction with the detailed description thereof, the foregoing description is intended to illustrate and not limit the scope of the invention, which is defined by the scope of to the appended claims. Other aspects, advantages, and modifications are within the scope of the following claims.

What is claimed is:

1. A method for reducing or mitigating, in a subject in need thereof, one or more deleterious effects of exposure to proton radiation, wherein the method comprises administering to the subject a composition comprising an active ingredient and one or more pharmaceutically acceptable excipients, wherein the active ingredient consists of nanoparticulate genistein, wherein the subject is identified as having been exposed to proton radiation or as being at risk of exposure to proton radiation, wherein the nanoparticulate genistein is present in the composition at a concentration between about 250 mg/mL and about 500 mg/mL and is effective to reduce or mitigate the one or more deleterious effects of proton radiation in the subject, and wherein the one or more deleterious effects are one or more of acute radiation syndrome (ARS), delayed effects of acute radiation syndrome, cardiovascular disease, tissue fibrosis, inflammation, and neurodegenerative conditions.

2. The method of claim 1, wherein the subject is a human.

3. The method of claim 1, wherein the subject is a cancer patient who will undergo proton radiation therapy.

4. The method of claim 1, wherein the genistein nanoparticulate composition has a particle size distribution characterized by a d(0.5) less than or equal to 0.5 μm.

5. The method of claim 1, wherein the one or more pharmaceutically acceptable excipients include a water soluble polymer comprising a polyvinylpyrrolidone.

6. The method of claim 1, wherein the composition comprises a diluent and a preservative.

7. The method of claim 1, wherein the nanoparticulate genistein is present in the composition at an amount ranging up to about 50% (w/w).

8. The method of claim 7, wherein the nanoparticulate genistein is present in the composition at an amount of about 20% to about 35% (w/w).

9. The method of claim 1, wherein the composition has a nanoparticulate genistein concentration of about 325 mg/mL.

10. The method of claim 1, wherein the composition is formulated as a tablet, a capsule, a pre-filled sachet, a gel cap, a powder, a granule, a suspension, or a solution.

11. The method of claim 1, comprising administering the composition orally, intramuscularly, subcutaneously, or intravenously.

12. The method of claim 1, wherein the subject is a cancer patient who will undergo proton radiation therapy, and wherein the method comprises administering the composition about 2 hours before exposure to the proton radiation therapy.

13. The method of claim 1, wherein the subject is a cancer patient who will undergo proton radiation therapy, and wherein the method comprises administering the composition within about 48 hours before exposure to the proton radiation therapy.

14. The method of claim 1, wherein the subject is a cancer patient who will undergo proton radiation therapy, and wherein the method comprises administering the composition within about 24 hours before exposure to the proton radiation therapy.

15. The method of claim 1, comprising administering the composition on a daily basis.

16. The method of claim 1, comprising administering the composition at a dose of about 0.5 g to about 2.5 g.

17. The method of claim 1, comprising administering the composition within about 60 minutes after exposure to the proton radiation.

18. The method of claim 1, comprising administering the composition within about 24 hours after exposure to the proton radiation.

19. The method of claim 1, comprising administering the composition at a dose of about 0.5 g to about 2.5 g per day for about 1 day to about 90 days.

20. The method of claim 1, comprising administering the composition two times a day.

* * * * *